United States Patent
Kuo

(10) Patent No.: US 11,966,366 B2
(45) Date of Patent: Apr. 23, 2024

(54) SYSTEMS AND METHODS FOR SECURING PRIVATE PATIENT DATA IN A CLINICAL DATA FILE

(71) Applicant: Align Technology, Inc., San Jose, CA (US)

(72) Inventor: Eric E. Kuo, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/892,013

(22) Filed: Aug. 19, 2022

(65) Prior Publication Data
US 2022/0405241 A1 Dec. 22, 2022

Related U.S. Application Data

(63) Continuation of application No. 16/270,891, filed on Feb. 8, 2019, now Pat. No. 11,436,191, which is a continuation of application No. 14/272,186, filed on May 7, 2014, now abandoned, which is a continuation of application No. 11/983,280, filed on Nov. 8, 2007, now Pat. No. 8,738,394.

(51) Int. Cl.
| | |
|---|---|
| *G16H 10/60* | (2018.01) |
| *G06F 16/16* | (2019.01) |
| *G06Q 10/10* | (2023.01) |
| *G16H 30/20* | (2018.01) |

(52) U.S. Cl.
CPC ............ *G06F 16/16* (2019.01); *G06Q 10/10* (2013.01); *G16H 10/60* (2018.01); *G16H 30/20* (2018.01)

(58) Field of Classification Search
CPC ...................................................... G16H 10/60
See application file for complete search history.

(56) References Cited

U.S. PATENT DOCUMENTS

| | | | |
|---|---|---|---|
| 7,001,270 B2 | 2/2006 | Taub | |
| 7,383,198 B1 | 6/2008 | Sepe | |
| 7,580,846 B2 | 8/2009 | Chishti et al. | |
| 7,860,342 B2 * | 12/2010 | Levien | ............... G06F 21/6254 |
| | | | 358/1.14 |
| 7,870,280 B2 | 1/2011 | Kuo | |
| 7,904,307 B2 | 3/2011 | Abolfathi et al. | |
| 8,024,198 B2 | 9/2011 | Kuo | |
| 10,467,815 B2 | 11/2019 | Marom et al. | |
| 10,695,150 B2 | 6/2020 | Kopelman et al. | |
| 10,888,399 B2 | 1/2021 | Kopelman et al. | |
| 10,980,612 B2 | 4/2021 | Jang | |

(Continued)

*Primary Examiner* — Sheetal R Paulson
(74) *Attorney, Agent, or Firm* — Shay Glenn LLP

(57) ABSTRACT

Method and systems for creating clinical data files with secured medical information. A clinical data file may be created by converting clinical data to a single format, and the medical information may be entered into corresponding data fields in the clinical data file. The medical information may include treatment professional information, patient personal information, and/or patient image(s). Each of the data fields may be associated with an indicator, where the indicator, when enabled, may be configured to secure at least a portion of the medical information in the corresponding data field. The secured clinical data file may be configured such that, once a pass code is entered, the patient image(s) are modifiable by the addition of modification(s) that are arranged as layer(s) saved separately from the patient image(s).

22 Claims, 4 Drawing Sheets

(56) References Cited

U.S. PATENT DOCUMENTS

| | | |
|---|---|---|
| 10,980,613 B2 | 4/2021 | Shanjani et al. |
| 2005/0159986 A1 | 7/2005 | Breeland et al. |
| 2007/0192137 A1* | 8/2007 | Ombrellaro ............ G06Q 10/10 600/300 |
| 2007/0260492 A1* | 11/2007 | Feied ..................... G16H 50/70 705/3 |
| 2008/0013727 A1* | 1/2008 | Uemura ................. H04N 1/448 380/243 |
| 2008/0288289 A1 | 11/2008 | Sah |
| 2020/0160947 A1 | 5/2020 | Rasovsky et al. |

* cited by examiner

SYSTEMS AND METHODS FOR SECURING PRIVATE PATIENT DATA IN A CLINICAL DATA FILE

CLAIM OF PRIORITY

This application is a continuation of U.S. patent application Ser. No. 16/270,891, filed Feb. 8, 2019, titled "SYSTEMS AND METHODS FOR ANONYMIZING PATIENT IMAGES IN RELATION TO A CLINICAL DATA FILE," now U.S. Pat. No. 11,436,191, which is a continuation of U.S. patent application Ser. No. 14/272,186, filed May 7, 2014, titled "PERSONAL DATA FILE," now U.S. Patent Application Publication No. 2014-0280376, which is a continuation of U.S. patent application Ser. No. 11/983,280, filed Nov. 8, 2007, titled "CLINICAL DATA FILE," now U.S. Pate. No. 8,738,394, each of which is incorporated herein by reference.

BACKGROUND

The present disclosure relates to devices, files, mediums, and methods for keeping medical information private. The present disclosure, for example, includes a data file, where a treatment professional can designate as private, at least a portion of the medical or other information therein.

In some instances, it is beneficial when planning an orthodontic treatment process to confer and discuss various possible treatment routes with other treatment professionals (e.g., specialists such as orthodontists, oral surgeons, periodontists, and/or general dentists). However, although patient data can now be sent almost instantaneously over the Internet, it can be desirable to keep patient medical information as well as treatment professional information private (e.g., hidden) from a conferring treatment professional.

In addition, in determining a treatment process, information can be gathered in many different file formats. For example, information can include two and/or three-dimensional images, digital and/or analog images, and/or digital and/or analog video of a patient's mouth and/or surrounding features. Also, text files can be generated, including notes, comments, prescription notes, and/or medical history. However, difficulties can arise in viewing and sending multiple types of files since each type of file may require that each treatment professional have special software for each type of file.

DETAILED DESCRIPTION

According to the present disclosure, systems, devices, files, and methods are provided for converting clinical data to a single format and creating a clinical data file including the clinical data in the single format. Also, in some embodiments, treatment professional information, patient personal information, and/or patient images designated as private included in the clinical data file can be provided upon entering a pass code. As used herein, "clinical data" refers to data generated in the process of treating a patient. For example, clinical data can include, but is not limited to, patient medical information (e.g., dental or other medical information) items including x-rays, two and/or three-dimensional (3-D) models of a medical patient's mouth, and/or digital and/or analog pictures of the patient's teeth. In addition, clinical data can include prescription notes and/or treatment professional comments.

Clinical data can also include other information generated when forming a treatment plan for the patient. For example, such other information can include information that is generated in instances where the treatment plan is to reposition the patient's teeth with a number of stages of incrementally moving teeth using a plurality of discrete appliances, where each appliance successively moves one or more of the patient's teeth by incremental amounts.

In some embodiments, methods of the present disclosure can be carried out by instructions stored in memory and executed by a processor in a computing device. The instructions can, for example, be included in a computing device readable medium. In such embodiments, a computing device readable medium can be any medium that can store computing device readable information thereon. Suitable examples include optically or magnetically readable forms of media, among others.

Figure 1:
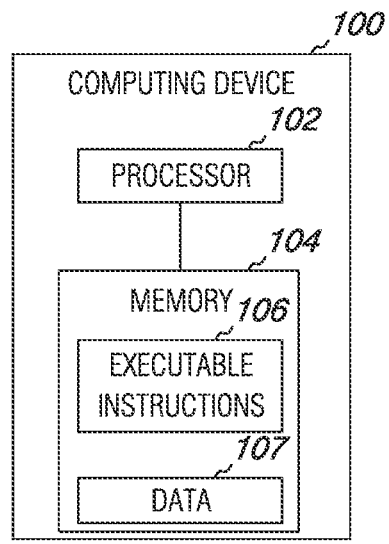
FIG. 1 illustrates a computing device embodiment to perform the methods of the present disclosure.

FIG. 1 illustrates a computing device embodiment to perform the methods of the present disclosure. In some embodiments, the computing device 100 can be used to create a clinical data file. In the computing device embodiment of FIG. 1, the device 100 includes one or more processors 102 in communication with one or more memory locations 104. The memory 104 can include a number of instructions 106 that can be executed on the processor 102. Memory 104 can also include one or more items of data 107 that can be used in the execution of the instructions 106 by the processor 102. The instructions 106 can, for example, be executed by the processor 102 to cause the computing device 100 to perform a method of the present disclosure, as described herein.

Figure 2:
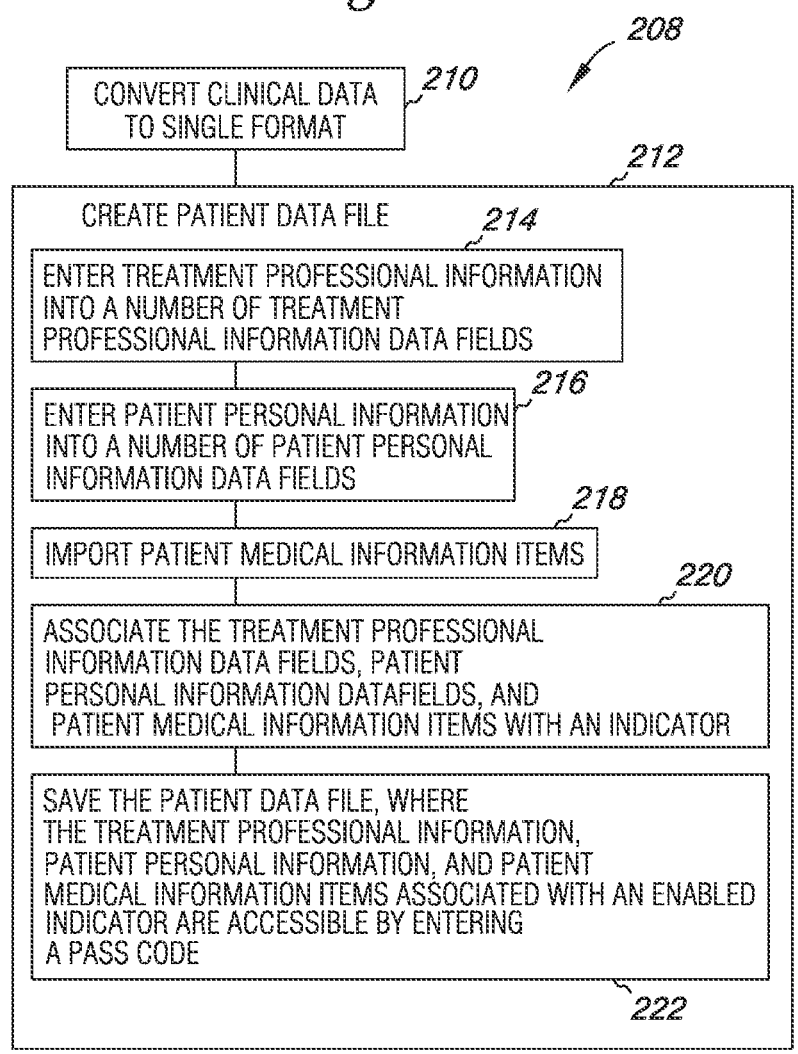
FIG. 2 illustrates a method for creating a clinical data file and securing medical information according to an embodiment of the present disclosure.

FIG. 2 illustrates a method for creating a clinical data file and securing medical information according to embodiments of the present disclosure. Unless explicitly stated, the method embodiments described herein are not constrained to a particular order or sequence. Additionally, some of the described method embodiments or elements thereof can occur or be performed at the same point in time.

As illustrated at block 210, the method 208 includes converting clinical data to a single format. In some embodiments, the conversion of clinical data can include converting all clinical data to a single format that is a different format than the clinical data is created in originally. For example, in some embodiments, the clinical data can be converted into a portable document format (PDF). In some embodiments, the conversion of clinical data can include converting a portion of the clinical data to a single format, where some clinical data is currently in the single format.

As illustrated at block 212, the method 208 includes creating a clinical data file 212 including the clinical data. As illustrated, creating the clinical data file 212 can include several steps.

For example, at block 214 treatment professional information can be entered into a number of treatment professional information data fields in a treatment professional profile section of the clinical data file. Treatment professional information can include, but is not limited to, treatment professional name, office address, office contact information (e.g., telephone number, fax number, electronic mail address), office logo, treatment professional photograph, practice mission/personal statement, and/or treatment professional resume highlights, among other items.

At block 216, patient personal information can be entered into a number of patient personal information data fields in a patient profile section of the clinical data file. The patient profile section can, for example, include, patient name, address, contact information (e.g., telephone number, fax number, electronic mail address), social security number, date of birth, gender, and/or insurance, among others.

At block 218, patient medical information items (e.g., patient images) can be imported into the clinical data file. In some embodiments, the patient medical information items can include several different types of patient images including x-ray, two or three-dimensional, and/or digital and/or analog images, among others.

In addition, in some instances, the various patient images may be created in many different file formats, making it difficult to view all of the patient images without specific software for each file format. By providing (e.g., converting) the clinical data (e.g., patient image) in a single format, and subsequently importing the patient images into the clinical data file, patient images that may have been created using different software can be viewed from the clinical data file using a single file viewer enabled by a single software application.

The many different types of patient images can include, for example, facial anterior (repose), facial anterior (smiling), profile (repose), profile (smiling), right buccal, left buccal, anterior intraoral, upper occlusal, lower occlusal, close-up smile, individual teeth, patient medical history (e.g., dental history), patient diagnosis, a three-dimensional (3-D) model of the patient's mouth (e.g., ClinCheck 3-D model, Invisalign® proprietary software that illustrates the movement of teeth), full mouth series x-rays, panoramic x-rays, cephalometric x-rays, and/or individual radiographs, among others. Since the patient images can include many different types of images, in some embodiments, creating the clinical data file 212 can include labeling the imported patient images according to data type (e.g., profile (smiling)).

In addition, in some embodiments, creating the clinical data file 212 can include positioning at least one patient image in a data file menu, as discussed further herein. For example, the patient images can be positioned in a hierarchy (e.g., a descending order) of importance according to a treatment professional. In some embodiments, instructions can be executed by the processor to put the imported images into a default position in the data file menu.

In some embodiments, at least one patient image can be represented by a thumbnail on the data file menu. In some such embodiments, instructions can be provided to select a thumbnail of a patient image which can initiate executable instructions to access an enlarged patient image and present the enlarged image on a display, among other functions.

As illustrated at block 220, creating the clinical data file 212 can include associating the treatment professional information data fields, patient personal information data fields, and/or patient medical information items with an indicator. The indicator functionality can be accomplished in various manners. For example, in some embodiments, the indicator can be a box that can be checked to enable the indicator.

In various embodiments, the indicator can be a drop down menu listing possible properties of the data field and/or information item. For example, the drop down menu properties can include, "hide information", "display information", and/or "secure information," among other suitable functions.

In such embodiments, when "hide information" is selected, the information contained in the data field and/or the information item, or portions thereof, can be hidden from a user viewing the clinical data file. When "display information" is selected, the information contained in the data field and/or the information item can be shown to the user viewing the clinical data file. When "secure information" is selected, the information contained in the data field and/or the information item can be shown by entering a pass code.

Also, as illustrated at block 222, the method 208 includes saving the clinical data file, where the treatment professional information, patient personal information, and/or patient medical information items associated with an enabled indicator can be accessed by entering a pass code.

In some embodiments, a method can include instructions executed by the processor to embed a pass code into the clinical data file once the clinical data file is saved in memory. For example, the pass code can be used to restrict viewing of some information (e.g., text/images, time based information, regions of images (e.g., eyes)), some files, and/or restrict transfer and/or modification of such information/files.

The pass code, for example, can be a password known to the user. The pass code can alternatively be an identifier associated with a computing device, such as an identifier uniquely associated with the computing device or network when the clinical data file is saved.

Further, a method can include instructions that are executed by the processor to allow the clinical data file to be modified after the pass code is entered into the computing device. By embedding a pass code into the clinical data file and preventing modifications to the clinical data file without the pass code, the clinical data file can be viewed by a limited number of users, however, only authorized users can modify the clinical data file. In addition, limiting modification ability can help to maintain the authenticity and integrity of the clinical data file.

In some embodiments, multiple pass codes can be used, where one pass code can allow modifications to the clinical data file and a second pass code can allow the ability to view the clinical data file without the ability to modify. Other pass codes can also be created to allow the viewing of specific items and/or areas of the clinical data file.

Once the clinical data file has been created and saved, instructions can be executed by the processor to view the clinical data file on a display. Viewing the clinical data file can include viewing the data file menu, the patient profile, and/or the treatment professional profile, among other things, as discussed herein.

Figure 3:
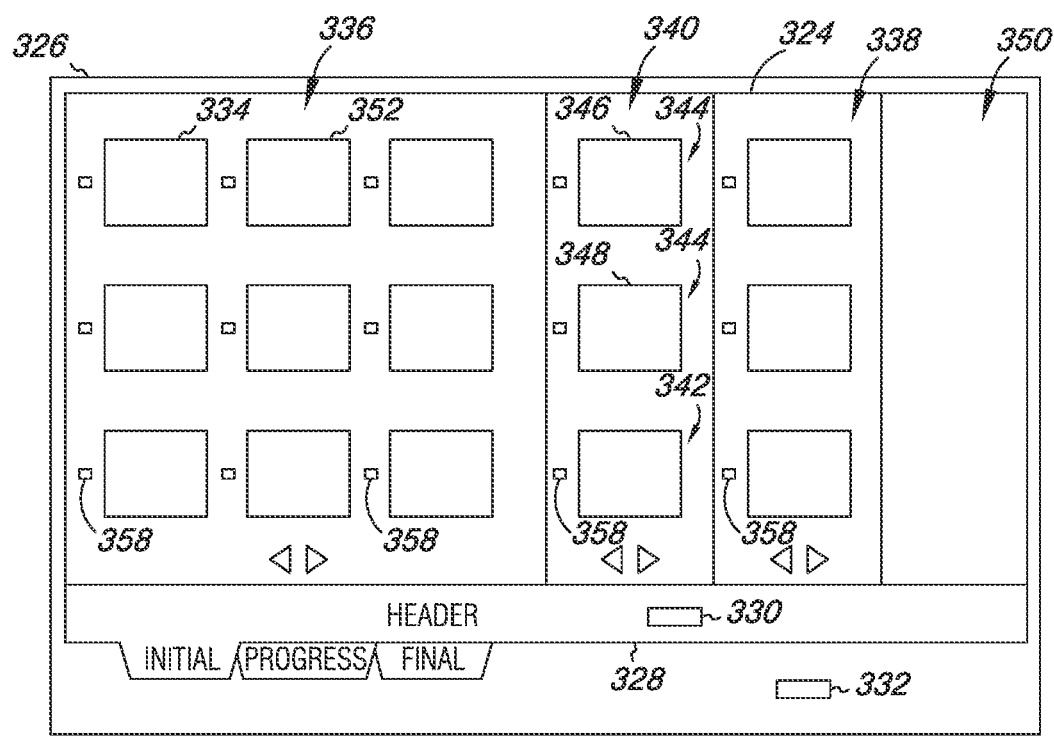
FIG. 3 is an illustration of a data file menu on a display according to an embodiment of the present disclosure.

FIG. 3 is an illustration of a data file menu 324 on a display 326 according to embodiments of the present disclosure. The data file menu 324 can include a header 328 displaying various patient personal information, such as a patient's name and age, among other items. For example, in some embodiments, the header 328 can display a patient's initials to maintain a patient's privacy, as discussed herein.

The header 328 can also include a patient personal information icon 330. When the patient personal information icon 330 is selected, instructions can be executed by the processor to view the patient profile section, as discussed herein.

In addition, the data file menu 324 can include a treatment professional information icon 332. Similarly, when the treatment professional icon 332 is selected, instructions can be executed by the processor to view the treatment professional profile section, as discussed herein.

In some embodiments, the patient images 334 can be separated into sections on the data file menu 324. For example, as shown in FIG. 3, patient images 334 that are photographs can be in a photograph section 336, patient images 334 that are x-rays can be in an x-ray section 338, and a third section 340 can include 3-D models 342 and text information 344.

In some embodiments, the text information 344 can be free text 346. In addition, as discussed herein, patient images 334 can include patient medical history. In some embodiments, the patient medical history can be a text image 348. In addition, in some embodiments, the data file menu 324 can include a comment section 350.

As discussed herein, in some embodiments, at least one patient image 334 can be associated with a thumbnail 352. As shown in FIG. 3, the data file menu 324 can include thumbnails 352 of the patient images 334 so that more images can be seen at one time.

In addition, when the patient image 334 is originally imported into the clinical data file, the patient image 334 and/or thumbnail 352 can be associated with an indicator 358. In some embodiments, the indicator 358 can be a box, as shown in FIG. 3, where the box can be "checked" to enable the indicator 358 when enabled executable instructions can be initiated to perform a function having to do with the image.

In some such embodiments, when an indicator 358 is enabled, instructions executable by the processor can hide the image 334 associated with the enabled indicator 358 when the clinical data file is being viewed by a user, as discussed herein. Therefore, when a user views the clinical data file, the user can see the data file menu 324 as illustrated in FIG. 3, without the indicators 358.

Figure 4:
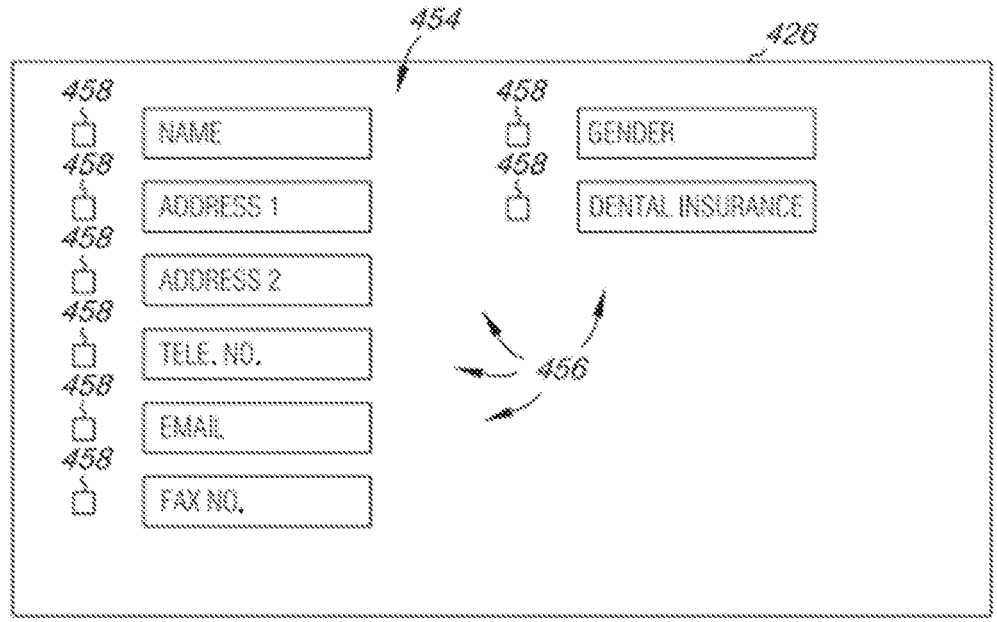
FIG. 4 is an illustration of a display of a patient profile section according to an embodiment of the present disclosure.

FIG. 4 is an illustration of a display 426 of a patient profile section 454 according to embodiments of the present disclosure. The patient profile section 454 illustrated shows the section 454 when the clinical data file is created.

In FIG. 4, the patient profile section 454 can include various data fields 456 that can be filled in with different types of information including, for example, name, address, telephone number, email, fax number, gender, and/or insurance, among others. When the patient personal information icon on the data file menu is selected by a user, other than the user (e.g., treatment professional) creating the clinical data file, the patient profile section 454 can be as illustrated without the indicators, as discussed herein.

Each patient personal data information data field 456 can be associated with an indicator 458. Similarly to the indicators 358 of FIG. 3, the indicators 458 can be of any suitable type. In some embodiments, the indicator 458 can be a box, as shown in FIG. 4, where the box can be "checked" to enable the indicator 458.

In such embodiments, when an indicator 458 is enabled, instructions executable by the processor can hide the information associated with the enabled indicator 458 when the clinical data file is being viewed by a user, as discussed herein. For example, when the indicator 458 associated with the patient's name is enabled, the patient's name can be hidden, and the patient's initials can be displayed in the data file menu, as discussed herein.

In some embodiments, the information associated with the enabled indicator 458 can be shown by entering a pass code, as discussed herein. In addition, in various embodiments, the indicator 458 can be a drop-down menu, where a user can select either "hide information," "display information," or "secure information" for each patient personal information data field 456.

In some embodiments, when a user selects the patient personal information icon on the data file menu, the patient profile can be displayed (e.g., as shown in FIG. 4 without the indicators 458), and the data fields associated with enabled indicators 458 can be displayed with, for example, the message "confidential information." In addition, data fields that are left blank when the clinical data file is created can be absent from the patient profile section 454. By distinguishing between a data field containing confidential information and a data field that is blank, a treatment professional can determine whether it would be useful to obtain permission to view the confidential information, rather than obtain permission to view confidential information only to find the data field blank.

Figure 5:
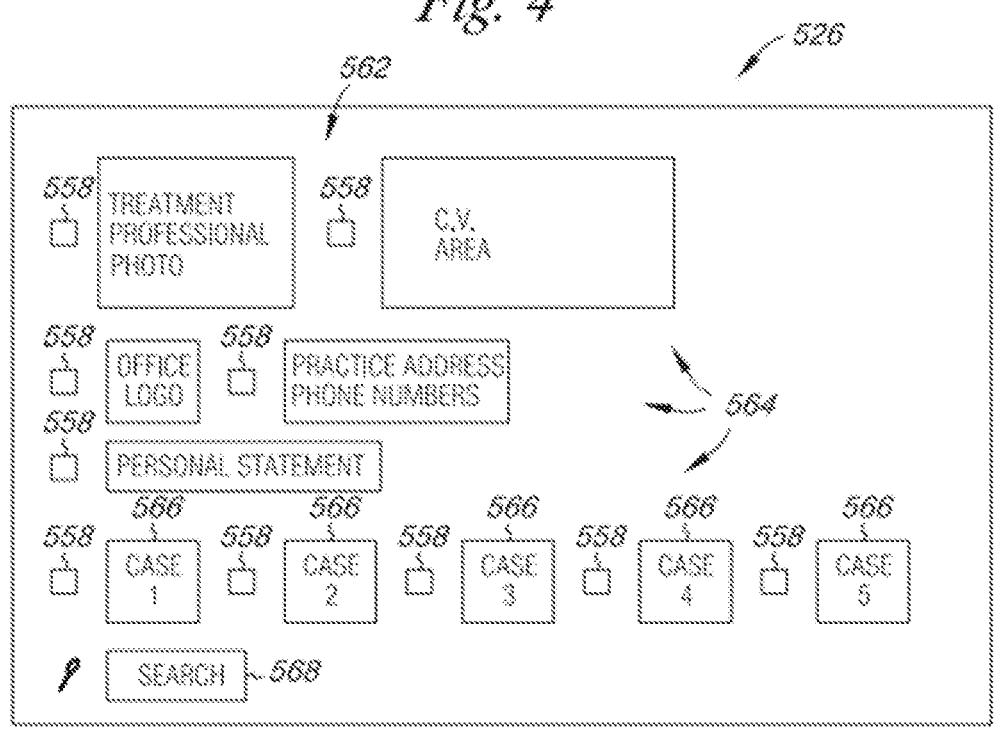
FIG. 5 is an illustration of a display of a treatment professional profile section according to an embodiment of the present disclosure.

FIG. 5 is an illustration of a display 526 of a treatment professional profile section 562 according to embodiments of the present disclosure. Similarly to the patient profile section (e.g., FIG. 4), the treatment professional profile section 562 illustrated shows the treatment professional profile section 562 when the clinical data file is created.

As discussed herein, when the treatment professional icon is selected, instructions can be executed by the processor to view the treatment professional profile section 562. The treatment professional profile section 562 can include various treatment professional data fields 564 that can be filled in with different types of information including, for example, a treatment professional photograph, a practice address and phone number, an office logo, a personal statement, consulting rates, and/or resume highlights, among others.

In some embodiments, the treatment professional profile section 562 can include sample cases 566 for a potential patient to view. The potential patient can select a sample case 566, where instructions executable by the processor can display a data file menu (e.g., FIG. 3), and the potential patient can see "before" and "after" images of, for example, a patient's teeth. The potential patient can then determine if the treatment professional is a good match for the particular treatment that the potential patient requires based on the sample cases 566.

In such embodiments, the clinical data file can include multiple treatment professional profiles including several sample cases 566. In addition, in some embodiments, the treatment professional profile section 562 can include a search tool 568. In such embodiments, the potential patient can enter a search term into the search tool 568, and instructions executable by the processor can display treatment professional profile sections 562 that include the search term.

In some embodiments, the treatment professional profile section 562 can include a rating indicating how much experience the treatment professional has with a certain treatment option. For example, the rating can indicate how much experience the treatment professional has with using technologies from Align Technology, Inc.

In addition, as discussed herein, in some embodiments, the treatment professional profile section 562 can include a data field 564 where the treatment professional can enter consulting rates. This information can be useful for a potential patient when selecting a treatment professional and/or a treatment professional seeking a second opinion.

In addition, the treatment professional can keep identifying information about the patients in the sample cases 566 private by enabling the indicators 558 associated with patient personal information data fields in the patient profile section, as discussed herein. Each treatment professional data field 564 can be associated with an indicator 558, as discussed herein with regard to the patient profile section (e.g., FIG. 4). When an indicator 558 is enabled, instructions executable by the processor can hide the information associated with the enabled indicator 558 when the clinical data file is being viewed by a user, as discussed herein.

In some embodiments, the information associated with the enabled indicator 558 can be shown by entering a pass code, as discussed herein. In addition, in various embodiments, the indicator 558 can be a drop-down menu, where a user can select either "hide information," "display information," or "secure information" for each treatment professional information data field 564.

In various embodiments, treatment professional information entered into data fields 564 associated with a disabled indicator 558 can be embedded into the clinical data file. In such embodiments, the treatment professional information can be unmodifiable except by the treatment professional, for example, by entering a pass code.

In some embodiments, when a user selects the treatment professional icon is selected on the data file menu, the treatment professional profile can be displayed (e.g., as shown in FIG. 5 without the indicators 558), and the data fields associated with enabled indicators 558 can be displayed with, for example, the message "confidential information." In addition, data fields that are left blank when the clinical data file is created can be absent from the treatment professional profile section 562, as discussed herein.

As discussed herein, when viewing the data file menu (e.g., FIG. 3), one or more patient images can be shown as a thumbnail. In addition, the thumbnail can be selected and instructions can be executable by the processor to enlarge the patient image.

Figure 6:
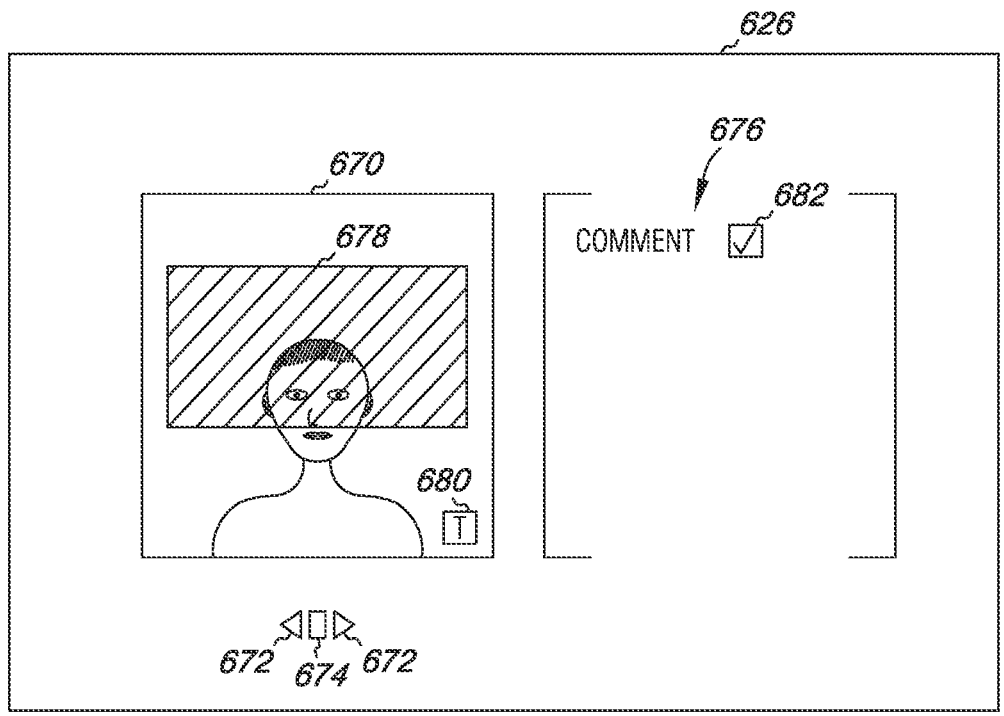
FIG. 6 is an illustration of a display of an enlarged patient image according to an embodiment of the present disclosure.

FIG. 6 is an illustration of a display 626 of an enlarged patient image 670 according to embodiments of the present disclosure. In some embodiments, the display 626 can include navigation arrows 672, where instructions can be executed by the processor to advance the enlarged patient image 670 from one image to the next patient image in the data file menu.

Instructions can also be executed to go back to the previous patient image in the data file menu when one of the navigation arrows 672 is selected. The display can also include a menu shortcut 674, where instructions can be executed by the processor to return to the data file menu (e.g., FIG. 3) when selected.

As illustrated in FIG. 6, the display of the enlarged patient image 670 can include a comments section 676 as discussed herein. In some embodiments, when the thumbnail of a patient image is selected, instructions can be executed by a processor to enlarge the patient image, as shown in FIG. 6, and to display comments associated with the patient image in the comment section 676.

In some embodiments, a patient image can include notations on the image. In some embodiments, a comment in the comment section 676 can explain the notation on the image.

In some embodiments, when the clinical data file is created and the patient images are imported, a user (e.g., treatment professional) can modify the patient image in various manners. For example, in some embodiments, modification can be accomplished by highlighting an area, by circling an aspect and/or area, and/or by including a privacy region 678. Such actions can be accomplished by executable instructions to perform and display such modifications.

FIG. 6 illustrates the privacy region 678 where an area of the enlarged patient image 670 is blacked out. Blacking out an area of a patient image can help a treatment professional hide identifying characteristics of a patient.

In some embodiments, the privacy region 678 can include an area of the patient image that is, for example, blurred rather than blacked out. In some embodiments, the privacy region 678 can be accessible by entering a pass code.

Including the privacy region 678 can allow a treatment professional to provide the clinical data file to a potential patient or to send the clinical data file to a second treatment professional for a second opinion without losing doctor-patient confidentiality. It can also allow the treatment professional to send the clinical data file over an unsecured internet connection (e.g., public email) while retaining the anonymity of the patient information included in the clinical data file. Including the privacy region 678 can also decrease the need for additional documentation between the treatment professional, patient, and second treatment professional regarding permission to view the clinical data file. In some embodiments, the user can include a comment in the comment section 676 explaining the modification and/or privacy region 678.

In some embodiments, the data file menu comment section (e.g., comment section 350 in FIG. 3) can include a list of comments such as comments regarding modifications to images and comments made by a treatment professional when creating and/or viewing the clinical data file, as discussed herein. In some embodiments, the comment section illustrated in FIG. 6 can include the list of comments displayed in the comment section on the data file menu.

In various embodiments, the comment section illustrated in FIG. 6 can include just the one or more comments associated with the enlarged patient image 670, as discussed herein. In some embodiments, the user can choose between viewing the entire list of comments from the data file menu or the comments associated with the enlarged patient image 670, or can select comments to be viewed.

As shown in FIG. 6, the enlarged patient image 670 can include a toolbar 680 for modifying the enlarged patient image 670. When the toolbar 680 is selected, instructions executed by the processor can cause tools to appear, such as, text tools, fill tools, and/or draw tools, including circle, square, pen size selection, and/or color selection, among others.

An exit tool can also appear when the toolbar 680 is selected, in some embodiments. In such embodiments, once the tools appear, a user can modify the enlarged patient image 670 to highlight an area of interest and/or to make a notation on the enlarged patient image 670, among other modifications.

Once the user is finished, the user can select the exit tool and instructions executable by the processor can save the modifications. In addition, the user can enter comments into the comment section 676, as discussed herein, explaining the modifications and/or inquiring about a portion of the enlarged patient image 670.

Other types of comments can also be entered into the comment section 676. For example, in some embodiments, instructions executable by the processor can save the modifications and/or the comments entered into the comment section 676 separate from the enlarged patient image 670. In addition, by entering comments into the comment section 676 with the enlarged patient image 670, instructions executed by the processor can associate the comments with the enlarged patient image 670 displayed when the one or more comments are entered.

As discussed herein, in some embodiments, the comments entered into the comment section 676 with the enlarged patient image 670 can also be seen on the data file menu in the comment section as a discussion thread. In embodiments where the comments entered are associated with the enlarged patient image 670 displayed when the comment is entered, a tag 682 can be inserted into the comment section 676 with the enlarged patient image 670 as well as next to the comment in the comment section on the data file menu.

As used herein, the tag 682 refers to an icon, where the icon can be a graphic picture (e.g., a pencil), and/or a textual hyperlink. In such embodiments, instructions can be executed by a processor to enlarge the modified patient image associated with the comment when the tag 682 is selected. In some embodiments, more than one modified patient image can be enlarged when multiple tags 682 are selected.

As discussed herein, in some embodiments, a treatment professional can send the clinical data file to a second treatment professional for a second opinion. In some embodiments, the second treatment professional can modify the enlarged patient images 670 and/or insert comments.

In such embodiments, by associating a tag with a comment when the comment is inserted after the enlarged patient image 670 is modified, the treatment professional can view the enlarged patient images 670 directly from the data file menu by selecting the tag 682 associated with the comment. This can help the treatment professional follow the order in which the second treatment professional viewed the clinical data file, facilitating greater understanding of the second opinion and the thought process to form the second opinion.

In some embodiments, once the user is finished modifying the enlarged patient image 670 and/or entering comments into the comment section 676 and selects the exit tool, instructions can be executed by the processor to secure the comments and/or modifications from further modification. In some embodiments, the comments and/or modifications can be modified after entering a pass code into the computing device.

In some embodiments, instructions are executed by the processor to send the clinical data file to a second computing device. In various embodiments, the clinical data file can be sent to a second user, as discussed herein, where the user can view the clinical data file on the same computing device, a second computing device, or an unnetworked computing device by transport of one or more files on a portable computing device readable medium.

For example, the clinical data file can be sent from a first treatment professional to a second treatment professional via the Internet. The second treatment professional can then open and view the clinical data file on a display at any computing device that includes a computing device readable medium having instructions which can be executed by a processor to cause a computing device to view the clinical data file.

In some embodiments, once the clinical data file is received, instructions which can be executed by a processor can cause the computing device to view the clinical data file menu (e.g., as shown in FIG. 3), on a display 626. The clinical data file menu can include, for example, one or more thumbnails of patient images, one or more tabs in a sequence of tabs, one or more comment sections, patient personal information, and/or treatment professional information, as discussed herein. In addition, a thumbnail can be selected to enlarge the patient image.

In such embodiments, the treatment professional or other user who receives the clinical data file can use the tool bar 680 to modify one or more enlarged patient images 670, and/or can enter comments into the comment section 676. As discussed herein, a tag 682 can be inserted in the comment section 676 when the comment is associated with the enlarged patient image 670 that is modified and/or that is displayed when the comment is entered. The treatment professional or other user can repeat this process for as many patient images as desired.

As discussed herein, the modifications and comments can be saved separately from the enlarged patient images 670. In such embodiments, the treatment professional, or other user, can send the modifications and comments to the computing device that the clinical data file was received from and/or to another computing device or save to a fixed or portable computing device readable medium. When the original computing device and/or different computing device receives the modifications and/or comments, instructions can be executed by the processor to allow the receiving user to accept or reject the modifications and/or comments.

In embodiments where the receiving computing device includes the clinical data file, accepting the modifications and/or comments can cause instructions executed by the processor to save the modifications and/or comments and merge them with the clinical data file. In embodiments where the receiving computing device does not include the clinical data file, accepting the modifications and/or comments can cause instructions executed by the processor to save the modifications and/or comments as well as the entire clinical data file. In some embodiments, the user sending the modifications and/or comments can choose whether to send the modifications, comments, and/or the entire clinical data file.

By saving the modifications and/or comments separately from the enlarged patient images 670, the enlarged patient image 670 as well as the clinical data file can be maintained in the form in which it was created. This can help to prevent unintended and/or unauthorized modifications to the clinical data file.

Allowing the user to accept or reject modifications and/or comments can also help to prevent unauthorized modifications. In addition, saving the modifications and/or comments separately from the enlarged patient images 670 can preserve the original, unaltered patient image, which may be important for medico-legal documentation purposes.

In some embodiments, the modifications and/or comments can be saved separately from the enlarged patient images 670 and arranged as layers on the enlarged patient images 670.

In such embodiments, the layers of modifications can be removed (e.g., by entering one or more pass codes) to revert to the original, unaltered patient image and other information. In other words, the enlarged patient images 670 and modifications and/or comments can be viewed separately, in some cases, by entering a pass code.

In some embodiments, more than one treatment professional, or other user, can send modifications and/or comments to the original treatment professional. In such embodiments, when the modifications and/or comments are accepted, instructions executed by the processor can cause more than one set of modifications and/or comments to be merged with the clinical data file.

In such embodiments, the different sets of modifications and/or comments can be displayed with an identifier to indicate the sender. For example, each treatment professional, or other user, sending modifications and/or comments can be assigned a different color, identifier, and/or font.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method for creating a clinical data file with secured medical information, the method comprising:
   creating a clinical data file by converting clinical data to a single format;
   entering medical information into corresponding data fields in the clinical data file, the medical information comprising one or more of: treatment professional information, patient personal information, and one or more patient images;
   associating each of the data fields with an indicator, wherein the indicator, when enabled, is configured to secure at least a portion of the medical information in the corresponding data field;
   displaying indicators associated with the data fields in a user interface;
   receiving instructions to enable at least one of the displayed indicators, wherein enabling the at least one of the displayed indicators secures at least a portion of the medical information in a corresponding at least one data field of the data fields; and
   saving a secured clinical data file with the secured at least a portion of the medical information in the corresponding at least one data field, wherein the secured at least a portion of the medical information is accessible by entering a pass code, wherein the secured clinical data file is configured such that, once the pass code is entered, the one or more patient images are modifiable by the addition of one or more modifications, wherein the one or more modifications are arranged as one or more layers that are saved separately from the one or more patient images.

2. The method of claim 1, wherein converting clinical data to the single format comprises converting the clinical data into a portable document.

3. The method of claim 1, wherein the treatment professional information includes one or more of: treatment professional name, office address, office contact information, office logo, treatment professional photograph, practice mission, personal statement, and treatment professional resume highlights.

4. The method of claim 1, wherein the patient personal information includes one or more of: patient name, address, contact information, social security number, date of birth, gender, and insurance.

5. The method of claim 1, wherein the one or more patient images include one or more of: a photograph, an x-ray image, a two-dimensional model, and a three-dimensional model of the patient's teeth.

6. The method of claim 1, wherein entering the medical information into the corresponding data fields in the clinical data file comprises labeling the one or more patient images according to data type.

7. The method of claim 1, wherein entering the medical information into the corresponding data fields in the clinical data file comprises positioning multiple patient images in a hierarchy of importance.

8. The method of claim 1, wherein entering the medical information into the corresponding data fields in the clinical data file comprises positioning the one or more patient images in a default position in the user interface.

9. The method of claim 1, further comprising displaying the one or more patient images as one or more thumbnail images in the user interface.

10. The method of claim 1, wherein displaying the indicators includes displaying a box that is configured to be checked to enable the indicator.

11. The method of claim 1, wherein displaying the indicators includes displaying a drop down menu configured to list possible ways to secure the medical information.

12. The method of claim 1, wherein the indicators include one or more of the following selectable options: hide information, display information, and secure information, wherein:
   when the hide information option is selected, the medical information contained in a corresponding data field, or a portion thereof, is configured to be hidden from a user viewing the secured clinical data file;
   when the display information option is selected, the medical information contained in a corresponding data field, or a portion thereof, is configured to be shown to the user viewing the clinical data file; and
   when the secure information option is selected, the medical information contained in a corresponding data field, or a portion thereof, is configured to be shown to the user viewing the clinical data file by entering the pass code, wherein the secured clinical data file is configured such that, once the pass code is entered, the one or more patient images are modifiable by the addition of one or more modifications, wherein the one or more modifications are arranged as one or more layers that are saved separately from the one or more patient images.

13. The method of claim 1, wherein securing at least a portion of the medical information in the corresponding at least one data field comprises adding a privacy region over at least a portion of the one or more patient images.

14. The method of claim 13, wherein the one or more layers include a privacy region that is saved over the one or more patient images.

15. The method of claim 1, further comprising receiving instructions to accept the one or more modifications, and merging the one or more modifications with the secured clinical data file in response to accepting the one or more modifications.

16. The method of claim 1, wherein saving the secured clinical file comprises associating different modifications of the one or more modifications with corresponding different users, and displaying different identifiers indicating the different modifications associated with the different users.

17. A system comprising:
one or more processors;
memory coupled to the one or more processors, wherein the memory includes computer-program instructions that, when executed by the one or more processors, cause the system to perform a computer-implemented method comprising:
  creating a clinical data file by converting clinical data to a single format;
  entering medical information into corresponding data fields in the clinical data file, the medical information comprising one or more of: treatment professional information, patient personal information, and one or more patient images;
  associating each of the data fields with an indicator, wherein the indicator, when enabled, is configured to secure at least a portion of the medical information in the corresponding data field;
  displaying indicators associated with the data fields in a user interface;
  receiving instructions to enable at least one of the displayed indicators, wherein enabling the at least one of the displayed indicators secures at least a portion of the medical information in a corresponding at least one data field of the data fields; and
  saving a secured clinical data file with the secured at least a portion of the medical information in the corresponding at least one data field, wherein the secured at least a portion of the medical information is accessible by entering a pass code wherein the secured clinical data file is configured such that, once the pass code is entered, the one or more patient images are modifiable by the addition of one or more modifications, wherein the one or more modifications are arranged as one or more layers that are saved separately from the one or more patient images.

18. The system of claim 17, wherein the one or more patient images include one or more of: a photograph, an x-ray image, a two-dimensional model, and a three-dimensional model of the patient's teeth.

19. The system of claim 17, wherein securing at least a portion of the medical information in the corresponding at least one data field comprises adding a privacy region over at least a portion of a corresponding patient image.

20. The system of claim 19, wherein the one or more layers include a privacy region that is saved over the one or more patient images.

21. The system of claim 17, wherein entering the medical information into the corresponding data fields in the clinical data file comprises labeling the one or more patient images according to data type.

22. The system of claim 17, wherein displaying the indicators includes displaying one or both of: a box and a drop down menu.

* * * * *